(12) United States Patent
Le Gette et al.

(10) Patent No.: US 6,332,223 B1
(45) Date of Patent: Dec. 25, 2001

(54) APPARATUS AND METHOD FOR MAKING AN EAR WARMER HAVING INTERIOR SEAMS

(75) Inventors: Brian Edward Le Gette, Severna Park; Justin Saul Werner, Millersville, both of MD (US)

(73) Assignee: Gray Matter Holdings, LLC, Baltimore, MD (US)

( * ) Notice: Subject to any disclaimer, the term of this patent is extended or adjusted under 35 U.S.C. 154(b) by 0 days.

(21) Appl. No.: 09/521,241

(22) Filed: Apr. 5, 2000

(51) Int. Cl.7 ......................................................... A42B 1/06
(52) U.S. Cl. ................................................. 2/209; 128/857
(58) Field of Search ..................................... 2/209; 128/857, 128/864, 866; 181/129, 137

(56) References Cited

U.S. PATENT DOCUMENTS 2,671,221  3/1954  Triplett .
4,660,229 * 4/1987 Harris .................................... 2/209
4,872,219 * 10/1989 Duncan ................................ 2/209
5,339,467 * 8/1994 Brinkley ............................... 2/209
5,545,859 * 8/1996 Ullrich ................................ 181/129
5,551,089 * 9/1996 Whidden .............................. 2/209
5,749,099 * 5/1998 Voorhees .............................. 2/209
5,821,468 * 10/1998 Urella et al. ...................... 181/129
6,065,157 * 5/2000 Felman ................................. 2/209
6,104,824  8/2000 Ito .

FOREIGN PATENT DOCUMENTS 10257581  8/2000  (JP) .

* cited by examiner

*Primary Examiner*—John J. Calvert
*Assistant Examiner*—Katherine Moran
(74) *Attorney, Agent, or Firm*—Cooley Godward LLP (57) ABSTRACT

An ear warmer comprises a set of membranes and a frame. The set of membranes collectively defines an outer perimeter. The set of membranes is attached along the outer perimeter to define an attachment portion. The attachment portion is entirely disposed within an interior of the set of membranes. The frame is disposed within the interior of the set of membranes.

31 Claims, 7 Drawing Sheets

APPARATUS AND METHOD FOR MAKING AN EAR WARMER HAVING INTERIOR SEAMS

BACKGROUND

The present invention relates to an ear warmer device. More specifically, the present invention relates to an apparatus and a method for making an ear warmer having interior seams.

U.S. Pat. No. 5,835,609 entitled "Ear Protection Device" relates to an ear warmer device having a shell that is constructed from multiple layers of fabric, and is incorporated herein by reference. The multiple layers of fabric are sewn along the collective perimeter of the fabric layers. The sewn seam is on the exterior of the ear warmer and can be covered by a binding sewn on top of the seam. A frame can be then inserted into the interior of the ear warmer shell formed by the sewn fabric layers to complete the assembly of the ear warmer.

Although the binding over the exterior-facing sewn seams provides an aesthetically pleasing appearance, the binding is an added expense and requires another step in the manufacturing process. Thus, it is desirable to provide a way to assemble the ear warmer without having exterior-facing sewn seams while also not requiring an additional component such as binding.

SUMMARY OF THE INVENTION

An ear warmer comprises a set of membranes and a frame. The set of membranes collectively defines an outer perimeter. The set of membranes is attached along the outer perimeter to define an attachment portion. The attachment portion is entirely disposed within an interior of the set of membranes. The flame is disposed within the interior of the set of membranes.

DETAILED DESCRIPTION

An ear warmer comprises a set of membranes and a frame. The set of membranes collectively defines an outer perimeter. The set of membranes is attached along the outer perimeter to define an attachment portion. The attachment portion is entirely disposed within an interior of the set of membranes. The frame is disposed within the interior of the set of membranes.

The term "attachment portion" is defined herein as a portion of the set of membranes between the attachment and the outer edge of the membranes. For example, the ear warmer membranes can be sewn together along their collective perimeter and then turned inside out. In such a case, the sewn seam as well as the extra portion of the membranes between the sewn seam and the outer edge of the membranes are inside the ear warmer; the frame can be inserted into the interior of the membranes.

Figure 1:
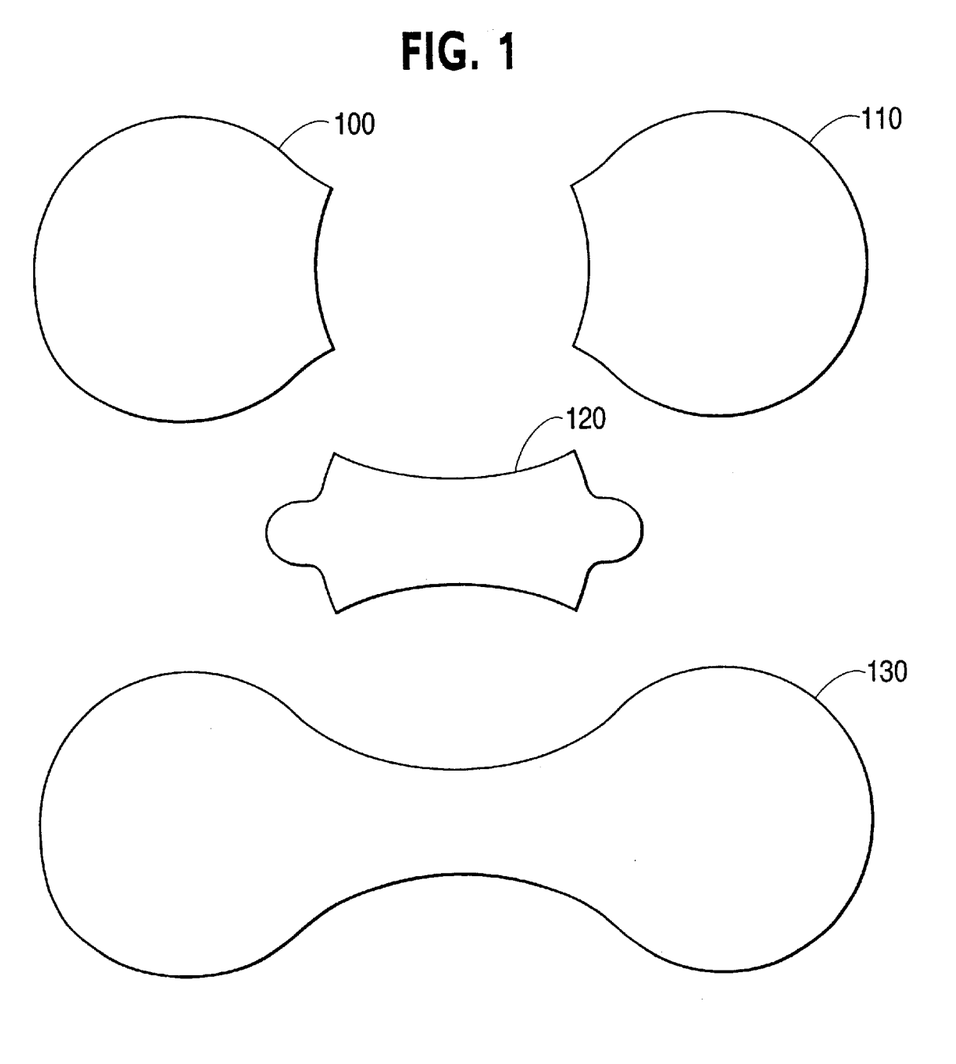
FIG. 1 illustrates a set of membranes for use in constructing an ear warmer, according to an embodiment of the present invention.

FIG. 1 illustrates a set of membranes for use in constructing an ear warmer, according to an embodiment of the present invention. As shown in FIG. 1, an ear warmer can be constructed from first ear membrane 100, second ear membrane 110, middle membrane 120 and outer membrane 130. Membranes 100 through 130 can be made of various types of material appropriate for providing warmth while also being comfortable on the wearer's skin. For example, membranes 100 through 130 can be made of such materials as fleece, wool, cotton, foam and/or neoprene.

Figure 2:
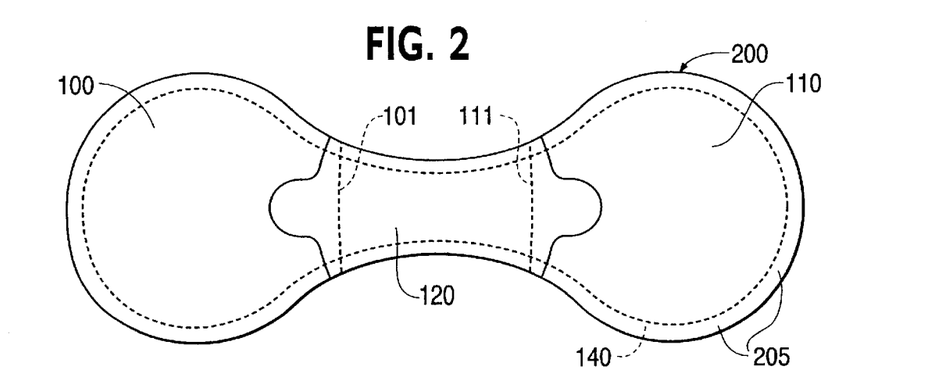
FIG. 2 illustrates an arrangement of an ear warmer shell during an interim step in an assembly process, according to an embodiment of the present invention.

FIG. 2 illustrates an arrangement of an ear warmer shell during an interim step in an assembly process, according to an embodiment of the present invention. Ear warmer shell 200 includes an arrangement of membranes 100 through 130 where they have been attached together via attachment 140 along the perimeter of the collection of membranes (i.e., along the perimeter of ear warmer 200). Attachment portion 205 is the portion of membranes 100 through 130 between and including attachment 140 and the edge of membranes 100 through 130. For example, when ear warmer membranes 100 through 130 are attached by sewing the membranes together along their collective perimeter, attachment portion 205 is the extra portion of the membranes between the sewn seam and the outer edge of the membranes.

More specifically, ear warmer shell 200 can be constructed by first disposing first ear membrane 100 and second ear membrane 110 on top of outer membrane 130. Middle membrane 120 can then be placed on top of the set of outer membrane 130, ear membrane 100 and ear membrane 110 in the arrangement shown in FIG. 2. Ear membranes 100 and 110, and middle membrane 120 are on top of each other and outer membrane 130 in the sense that they are ordered in a particular way; the particular orientation of the collection of membranes as shown in the figures herein are not important. The arrangement of membranes 100 through 130 can then be attached along the perimeter of ear warmer 200 via attachment 140. A portion of the perimeter of ear membrane 100 is not attached to outer membrane 130; this unattached perimeter portion is labeled as 101. Similarly, a portion of the perimeter of ear membrane 110 is not attached to outer membrane 130; this unattached perimeter portion is labeled as 111.

Figure 3:
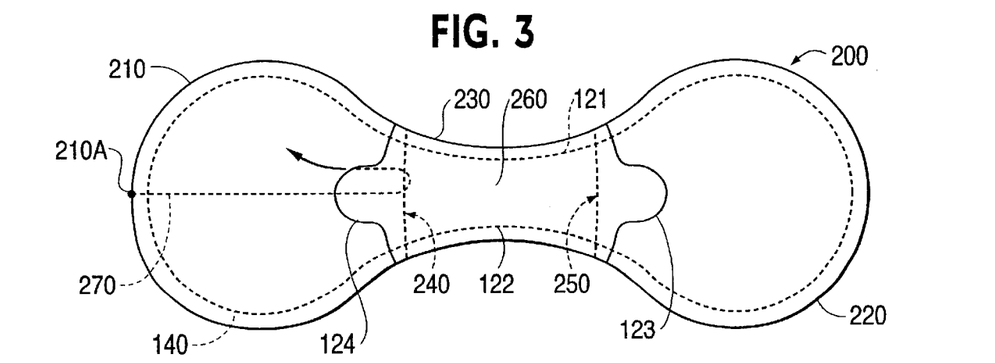
FIGS. 3, 4 and 5 illustrate top views of the ear warmer shell of FIG. 2 at different steps in a method for assembling an ear warmer, according to an embodiment of the present invention.

FIGS. 2, 3, 4 and 5 illustrate ear warmer shell 200 at different steps in a method for assembling an ear warmer, according to an embodiment of the present invention. As shown in FIG. 3, ear warmer shell 200 includes a first ear portion 210, a second ear portion 220 and a middle portion 230. First ear portion 210 includes opening 240 that is formed by the perimeter portion 101 of ear membrane 100. Similarly, second ear portion 220 includes opening 250 that is formed by the perimeter portion 111 of ear membrane 110.

Channel 260 is formed by middle portion 120 and the portion of outer membrane 130 disposed with middle membrane 120. More specifically, middle membrane 120 is attached along two portions 121 and 122 of its perimeter to outer membrane 130 while the two remaining portions 123 and 124 of the perimeter of middle membrane 120 are not attached to outer membrane 130. These unattached perimeter portions of middle membrane 120 generally correspond to openings 240 and 250, thus channel 260 is formed between the attached perimeter portions of middle membrane 120 from opening 240 to opening 250.

Figure 4:
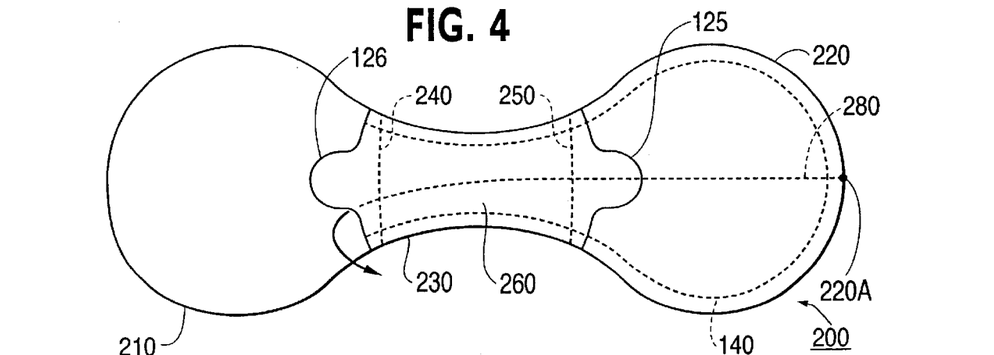

As shown in FIG. 3, ear portion 210 can be turned inside out through opening 240. More specifically, line 270 shows the direction in which ear portion 210 should be moved to turn it inside out. The outer edge 210A of ear portion 210 is moved through opening 240 so that ear portion 210 is turned inside out. In other words, an interior formed by ear membrane 100 and outer membrane 130 is turned outward by moving the end 210A of ear portion 210 along line 270 through opening 240 and then completely turned outward as shown in FIG. 4. In this manner, attachment 140 (e.g., an externally sewn seam) along the perimeter of ear portion 210 is turned inward so that a portion of the attachment 140 is located within a newly defined interior portion of ear portion 210. Consequently, this portion of attachment 130 is not visible from the outside of ear warmer shell 200, and rather is internal to ear warmer shell 200.

FIG. 4 illustrates another step for assembling an ear warmer according to an embodiment of the present invention. The outer edge 220A of ear portion 220 is turned inside out along line 280 so that the outer edge of ear portion 220 is moved through channel 260 and through opening 240. Once ear portion 220 is partially turned inside out within channel 260, it can be further moved along motion line 280 through the use of an additional device such as a dowel so that ear portion 220 can completely transit the channel 260 and be moved through opening 240.

Note that as ear portion 220 is turned inside out as described above in reference to FIG. 4, the middle portion 230 is also turned inside out. In other words, as the outer edge of ear portion 220 is turned inside out, the middle portion 230 is moved through its channel 260 and through opening 240. Consequently, middle portion 230 is turned inside out so that the exterior sides of middle portion 230 as shown in FIGS. 2 and 3 are now interior to ear warmer shell 200 as shown in FIG. 4.

Figure 5:
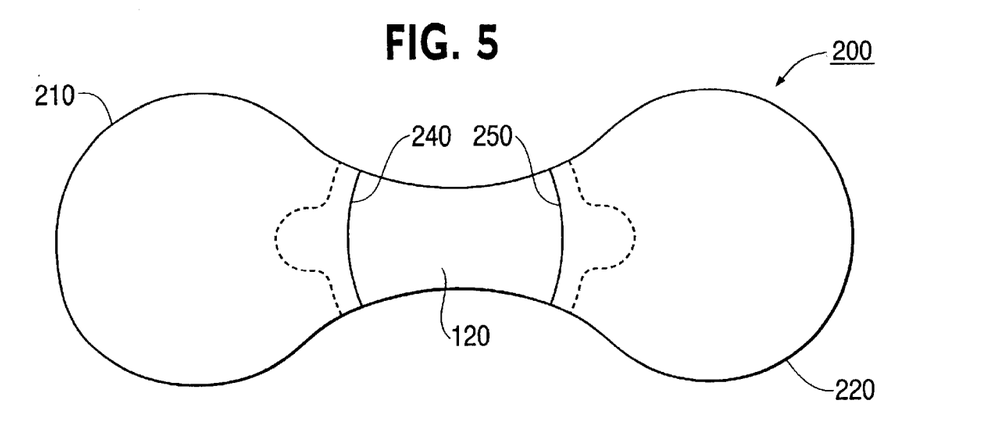

The unattached portions 125 and 126 of middle membrane 120 can then be placed through the respective openings 240 and 250 so that the ends of middle membrane 120 (shown, for example, as having tabs in FIGS. 3–5) are not visible from the outside but rather are disposed within the interior formed by ear membrane 100 and outer membrane 130 on one side of ear warmer shell 200 and formed by ear membrane 110 and outer membrane 130 are on the other end of ear warmer shell 200. Thus, as shown in FIG. 5, attachment 140 (e.g., the sewn seams) that was externally visible as the membranes were initially attached along the outer perimeter of ear warmer shell 200 (as illustrated, for example, in FIG. 2) are now all internal to ear warmer shell 200 and not visible from the exterior as shown in FIG. 5. In such a case, ear warmer shell 200 has a different appearance from that disclosed in U.S. Pat. No. 5,835,609 while yet being an aesthetically pleasing appearance and also obviating the need for binding over an external seam.

Figure 6:
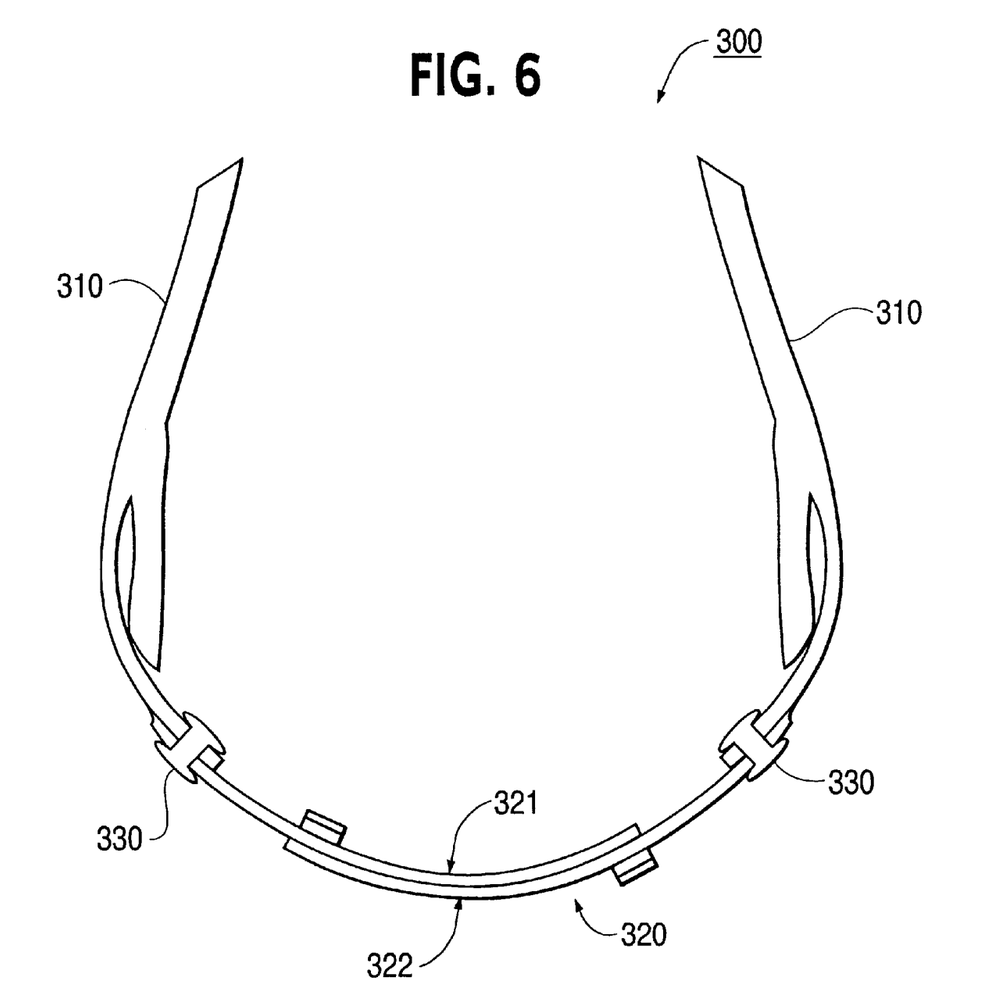
FIG. 6 illustrates a top view of a frame that can be disposed within an ear warmer shell to form an ear warmer, according to an embodiment of the present invention.

FIG. 6 illustrates a top view of a frame that can be disposed within an ear warmer shell to form an ear warmer, according to an embodiment of the present invention. Frame 300 includes a first frame member 310, a second frame member 310 and a third frame member 320. Frame member 320 can be, for example, a slidably adjustable band having an inner curved side 321 and an outer curved side 322. U.S. Pat. No. 5,835,609 discloses an example of frame 300 including frame members 310 and 320 and is incorporated herein by reference (see, e.g., FIGS. 28–38 and the associated written description in U.S. Pat. No. 5,835,609). Connection device 330 (such as a rivet) can attach frame members 310 to frame member 230.

Figure 7:
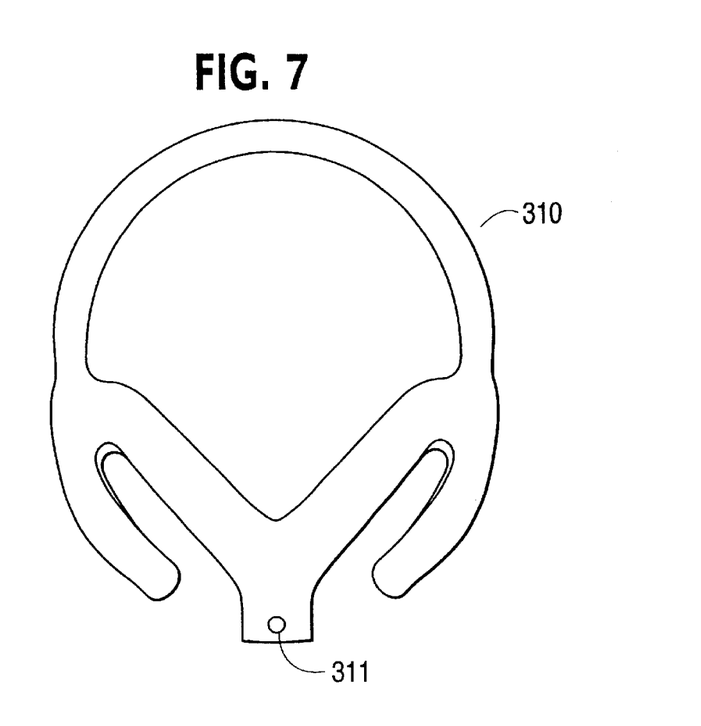
FIG. 7 illustrates a frame member of a frame to be inserted into an ear warmer shell, according to an embodiment of the present invention.

FIG. 7 illustrates a frame member of a frame to be inserted into an ear warmer shell, according to an embodiment of the present invention. More specifically, frame member 310 can have a frusto-conical shape that is conducive to being comfortably placed against a user's ear. Frame member 310 can include a connection portion 311. In the embodiment shown in FIG. 7, the connection portion 311 can include a rivet hole that aligns with a similar rivet hole in third frame member 320 (shown in FIG. 6); connection device 330 can then attach frame members 310 to frame member 320 via their respective connection portions 311. Alternatively, a connection portion of a frame member (similar in function to connection portion 311 and connection device 330 of frame member 300) can be an integral snap-fit connector that complementarily fits with an associated portion on a band-like frame member (similar to frame member 320).

The unattached frame members of frame 300 can be inserted into ear warmer shell 200 and then attached together by the following steps. First, a frame member 310 can be inserted into ear portion 210 through opening 240. Similarly, a second frame member 310 can be inserted in ear portion 220 through opening 250. Of course, frame members 310 can be oriented with respect to the membranes (and the wearer's head) appropriately; for example, outer membrane 130 can be positioned along the rear, outward facing (i.e., not adjacent to the wearer's head) with respect to the ear warmer. In such a case, the frame members 310 should be inserted into the respective interiors of ear portions 210 and 220 such that the relative base of the frusto-conical shape of frame members 310 is disposed towards the wearer's ears (i.e., the curvature of frame member 310 is similar to the wearer's head). Similarly, middle membrane 120 should be disposed inwardly adjacent to the wearer's head when the ear warmer is completely assembled and worn by the wearer.

In the next step in the method for inserting the frame, frame member 320 can be inserted into channel 260 through either opening 240 or 250. Again, frame member 320 should be disposed within channel 260 so that the curvature of frame member 320 is similar to the curvature of the user's head.

The ends of frame members 310 can be connected to the respective ends of frame member 320. Once frame members 310 and frame member 320 are appropriately positioned within the interior of ear warmer shell 200, connection portion 311 of frame member 310 can be disposed through opening 240 along with the corresponding end of frame member 320 so that frame member 310 and frame member 320 can be attached by connection devices 330. The other end of frame member 320 can likewise be attached to the other frame member 310.

Once the three frame members are attached to form frame 300, the ear warmer shell 200 can be arranged so that frame 300 is completely disposed within the interior ear warmer shell 200 and is not visible from the exterior. This can be accomplished, for example, by disposing the respective connected ends of frame members 310 and frame member 320 back into the interior ear warmer shell 200. The tab-like ends of middle membrane 120 can then be reinserted into openings 240 and 250 so that the assembling of the ear warmer including its ear warmer shell 200 and frame 300 is complete.

Figure 8:
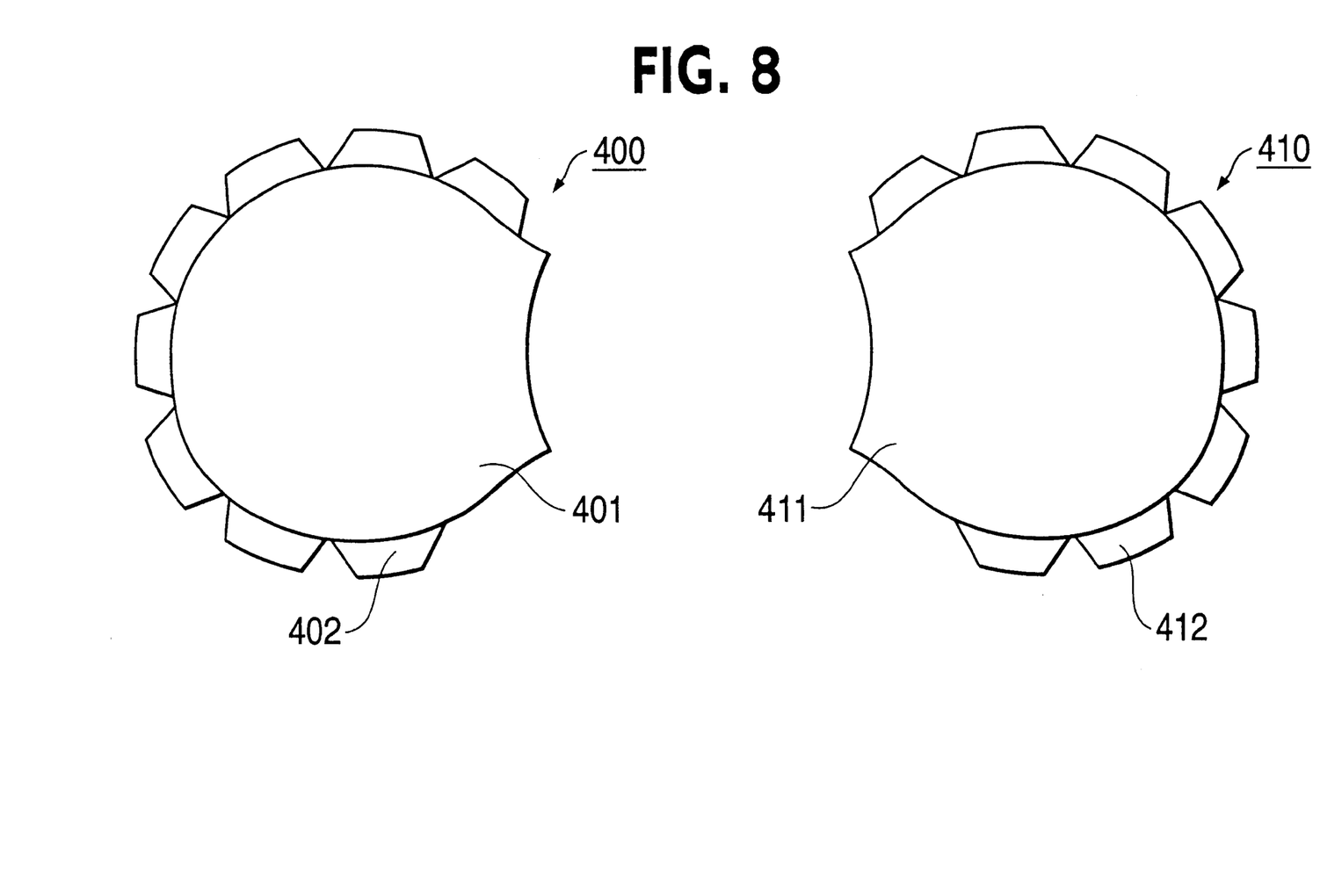
FIG. 8 illustrates ear membranes according to an alternative embodiment of the present invention.

FIG. 8 illustrates ear membranes according to an alternative embodiment of the present invention. Ear membrane 400, as shown in FIG. 8, includes central portion 401 and extended portions 402. Likewise, ear membrane 410 includes central portion 411 and extended portions 412. Note, although only one extended portion is labeled as 402 for ear membrane 400 and, similarly, only one extended portion is labeled 412 for ear membrane 410 in FIG. 8, this notation in FIG. 8 is merely for convenience and would apply to one or more extended portions as appropriate.

Ear membranes 400 and 410 can be substituted for ear membranes 100 and 110 as described in the apparatus and method described above in reference to FIGS. 1–7. In such an embodiment, the perimeter seams discussed in conjunction with FIG. 2 above would be formed along the partial perimeter of central portion 401 and 411 of ear membranes 400 and 410, respectively. In other words, extended portions 402 and 412 of ear membranes 400 and 410, respectively, are disposed outside of the collective perimeter for the ear warmer shell.

When the ear warmer shell is then turned inside out, for example as discussed above in reference to FIGS. 3–5, the extended portions 402 and 412 of ear membranes 400 and 410, respectively, are located within the interior of the ear warmer shell and form an additional layer of fabric. For example, FIG. 9 illustrates the extended portions of the ear membranes forming an added layer of fabric within the interior of the ear warmer shell.

Figure 9:
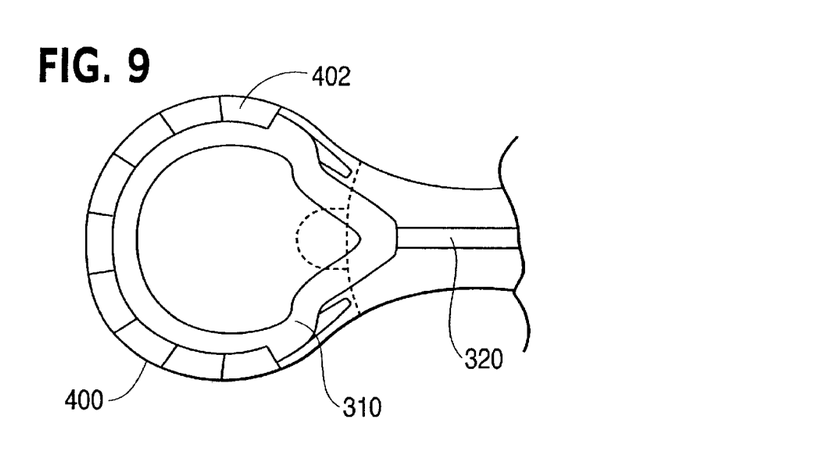
FIG. 9 illustrates a top view of a left portion of an ear warmer, according to an embodiment of the present invention.

More specifically, FIG. 9 illustrates a left portion of an ear warmer, according to an embodiment of the present invention. As illustrated in FIG. 9, the ear portion of the left side of FIG. 9 has the extended portions 402 (shown in phantom) of ear membrane 400 being disposed within the interior of an ear warmer shell such that they form a nearly continuous piece of additional fabric. In such a case, the frame member 310 (shown in phantom) when inserted into an interior of an ear warmer shell can be disposed between extended portions 402 and outer membrane 130. In such an embodiment, extended portions 402 provide an extra layer of cushioning fabric that is disposed between frame member 310 and the wearer's head. In other words, in such an embodiment, extended portions 402 and 412 in addition to central portions 401 and 411 of ear membranes 400 and 410, respectively, are disposed between the wearer and the frame member 310.

Figure 10:
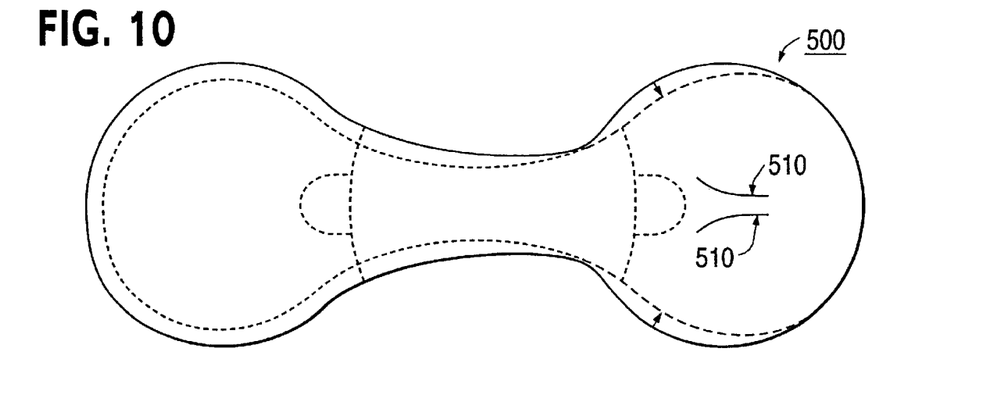
FIG. 10 illustrates a top view of an ear warmer shell, according to another embodiment of the present invention.

FIG. 10 illustrates an ear warmer shell according to another embodiment of the present invention. In such an embodiment of ear warmer shell 500, the ear membranes can have a size slightly smaller than the corresponding portions of the outer membrane. The extra material of the outer membrane portions corresponding to the ear membranes allows the frame(once inserted into the ear warmer shell) to better fit within the ear warmer shell 500. In other words, because the frame to be inserted into the ear warmer shell is curved, the outer curved side (e.g., outer curved side 322 as shown in FIG. 6) of the frame is a greater distance than the inner curved side (e.g., inner curved side 321 as shown in FIG. 6) of the frame. Thus, the extra material of the outer membrane allows the ear warmer shell 500 to better fit around the curved shape of the frame.

The method to construct ear warmer shell 500 is similar to that described above in reference to FIGS. 2–5. Before attaching (e.g., by sewing) the collective perimeter of the membranes, the portion of the outer membrane corresponding to an ear membrane can be pinched inwardly along lines 510 to gather the perimeter of the outer membrane to more closely match the corresponding perimeter of the ear membrane. For example, the portion of the outer membrane corresponding to an ear membrane can be pinched and held inwardly with a clip (such as a binder clip), then the collective perimeter of the membranes can be attached. Thus, collective perimeter of the membranes are aligned when the membranes are being attached while allowing the outer membrane to have extra material so that the frame can better fit within the ear warmer shell 500.

Figure 11:
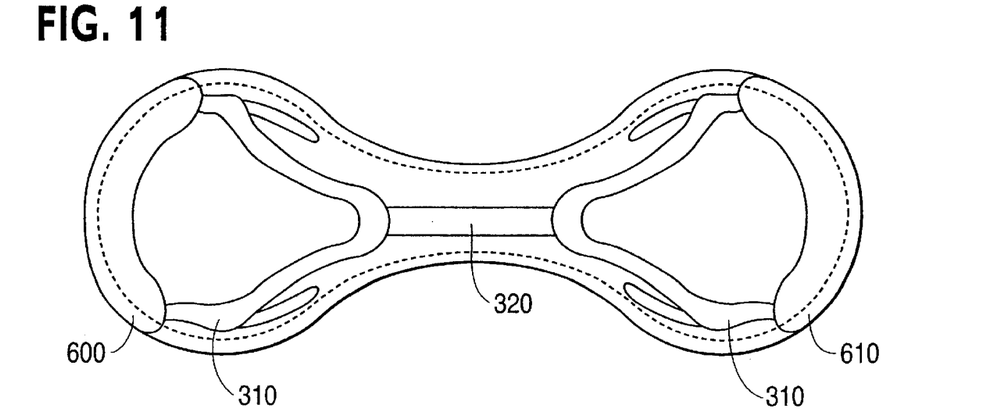
FIG. 11 illustrates internal components of an ear warmer shell, according to yet another embodiment of the present invention.

FIG. 11 illustrates internal components of an ear warmer shell, according to yet another embodiment of the present invention. For purposes of clarity, a covering portion of the ear warmer has been removed to show the internal components of the ear warmer. In this embodiment of an ear warmer shell, pocket membranes 600 and 610 (shown in phantom) are included. In such an embodiment, these additional and separate membranes, i.e., pocket membranes 600 and 610, can be attached (shown in phantom) along the respective portions of the collective perimeter of the ear warmer shell. In other words, pocket membranes 600 and 610 are attached to respective portions of outer membrane 130 and each form a respective pocket into which a frame member 310 can be inserted. The pocket membranes 600 and 610, provide additional cushioning between frame members 310 (shown in phantom) and the head of the user. In such an embodiment, pocket membranes 600 and 610 would be attached on top of the respective ear membranes. Thus, when the ear warmer shell is turned inside out (as described above, for example, in reference to FIGS. 3–5), pocket membranes 600 and 610 are appropriately positioned within the ear warmer shell.

Figure 12:
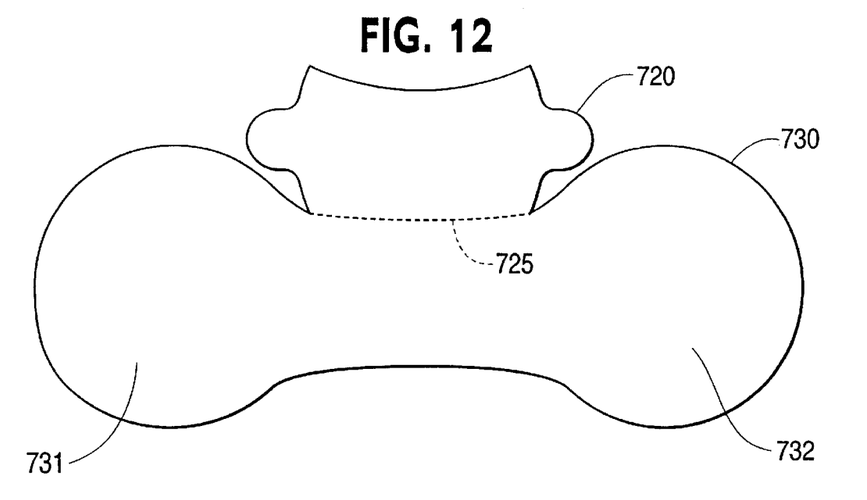
FIG. 12 illustrates a set of membranes for use in constructing an ear warmer, according to another embodiment of the present invention.

FIG. 12 illustrates a set of membranes for use in constructing an ear warmer, according to another embodiment of the present invention. Similar to the outer membrane 130 and the middle membrane 120 shown in FIG. 1, FIG. 12 illustrates a membrane having an outer portion 730 and a middle portion 720. The membranes can be arranged as follows. First, the ear membranes (e.g., ear membranes 100 and 110) can be placed on the corresponding portions of outer portion 730, i.e., portions 731 and 732 of outer portion 730. Middle portion 720 can then be folded on to outer portion 730 along the line 725. The collective perimeter can then be attached and the membranes can be turned inside out as described above in reference to FIGS. 3–5.

Figure 13:
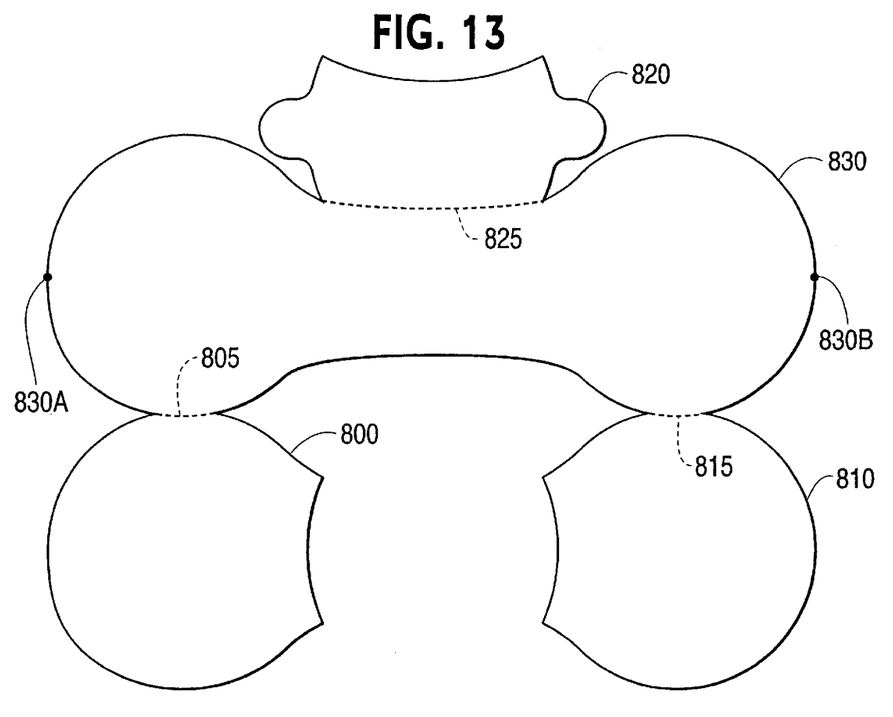
FIG. 13 illustrates a membrane for use in constructing an ear warmer, according to yet another embodiment of the present invention.

FIG. 13 illustrates a membrane for use in constructing an ear warmer, according to yet another embodiment of the present invention. Similar to ear membrane 100, ear membrane 110, middle membrane 120 and outer membrane 130 shown in FIG. 1, FIG. 13 illustrates a membrane having ear portion 800, ear portion 810, middle portion 820 and outer portion 830. The membrane portions can be arranged as follows. First, the ear portions 800 and 810 can be folded on to the corresponding portions of outer portion 830 along lines 805 and 815, respectively. Middle portion 820 can then folded on to outer portion 830 along the line 825. The collective perimeter can then be attached and the membranes can be turned inside out as described above in reference to FIGS. 3–5.

Rather than the separate membranes shown in FIG. 1, variations to FIGS. 12 and 13 are possible where certain membranes are integrally formed together and folded over. For example, in another embodiment, only one ear membrane is integrally formed with the outer membrane, only two ear membranes are integrally formed with the outer membrane, or only one ear membrane and the middle membrane are integrally formed with the outer membrane.

In another alternative embodiment, the membranes can be integrally formed together at various locations (e.g., discontinuous locations) rather than along the entire fold (such as line 725 shown in FIG. 12). In yet another embodiment, the membranes can be integrally formed at various locations relative to the outer portion of the membrane. For example, rather than the ear portions being integrally formed at the lower location of the outer portion (as shown in FIG. 13), the ear portions can be integrally formed with the outer portion at other locations, such as the side locations 830A and 830B of the outer portion. The various locations that are possible are those where the portions of the membrane (i.e., the middle portion, and/or the ear portions) fold on to the outer portion of the membrane to appropriately form the ear warmer shell.

It should, of course, be understood that while the present invention has been described in reference to particular configurations, other configurations will be apparent to those of ordinary skill in the art. For example, the membranes and frame members can be made of any type of materials appropriate for an ear warmer device. U.S. Pat. No. 5,835,609, which is incorporated herein by reference, discloses various embodiments of the ear warmer device and those variation can be combined with the method and apparatus described herein.

What is claimed is:

1. A method for assembling an ear warmer having a plurality of membranes, the plurality of membranes being attached along an outer perimeter, the plurality of membranes defining a first ear portion, a second ear portion and a middle portion, said method comprising:

turning inside out the first ear portion through an opening of the first ear portion; and turning inside out the second ear portion through an opening of the second ear portion, through a channel of the middle portion and through the opening of the first ear portion.

2. The method of claim 1, further comprising:

inserting a first frame member into the first ear portion through the opening of the first ear portion;

inserting a second frame member into the second ear portion through the opening of the second ear portion; and inserting a third frame member into the channel of the middle portion.

3. The method of claim 2, further comprising:

attaching a first end of the first frame member to a first end of the third frame member; and attaching a first end of the second frame member to a second end of the third frame member.

4. The method of claim 2, further comprising:

disposing a first end of the first frame member adjacent to a first end of the third member through the opening of the first ear portion;

attaching the first end of the first frame member to the first end of the third frame member;

disposing a first end of the second frame member adjacent to a second end of the third member through the opening of the second ear portion; and attaching the first end of the second frame member to the second end of the third frame member.

5. The method of claim 2, wherein the third frame member is a band having a slidably adjustable length.

6. The method of claim 1, further comprising:

attaching the plurality of membranes along an entirety of the outer perimeter.

7. The method of claim 1, further comprising:

attaching the plurality of membranes along an entirety of the outer perimeter before said turning the first ear portion and before said turning the second ear portion.

8. A method for assembling an article having a plurality of membranes, the plurality of membranes being fixedly attached along an outer perimeter, the plurality of membranes defining a first end portion, a middle portion and a second end portion, said method comprising:

turning inside out the first end portion through an opening of the first end portion; and turning inside out the second end portion through an opening of the second end portion, through a channel of the middle portion and through the opening of the first end portion.

9. The method of claim 8, wherein the plurality of membranes includes:

a first membrane; and a second membrane having a substantially oval shape and having a perimeter including a first perimeter portion and a second perimeter portion, the second membrane and the first membrane being fixedly attached along the first perimeter portion of the second membrane, the second membrane and the first membrane forming the opening of the first end portion along the second perimeter portion of the second membrane.

10. The method of claim 9, wherein the plurality of membranes further includes:

a third membrane having a substantially oval shape and having a perimeter including a first perimeter portion and a second perimeter portion, the third membrane and the first membrane being fixedly attached along the first perimeter portion of the third membrane, the third membrane and the first membrane forming the opening of the second end portion along the second perimeter portion of the third membrane.

11. The method of claim 8, wherein the plurality of membranes includes:

a first membrane, a second membrane having a substantially oval shape and having a perimeter including a first perimeter portion and a second perimeter portion, the second membrane and the first membrane being fixedly attached along the first perimeter portion of the second membrane, the second membrane and the first membrane forming the opening of the first end portion along the second perimeter portion of the second membrane, a third membrane having a substantially oval shape and having a perimeter including a first perimeter portion and a second perimeter portion, the third membrane and the first membrane being fixedly attached along the first perimeter portion of the third membrane, the third membrane and the first membrane forming the opening of the second end portion along the second perimeter portion of the third membrane, and a fourth membrane having a first perimeter portion, a second perimeter portion, a third perimeter portion and a fourth perimeter portion, the fourth membrane and the first membrane being fixedly attached along the second perimeter portion and the fourth perimeter portion of the fourth membrane, the first perimeter portion and the third perimeter portion of the fourth membrane forming two ends of the channel of the middle portion.

12. An ear warmer shell, comprising:

an outer membrane defining a perimeter;

a first ear membrane attached to said outer membrane along a first portion of the perimeter and defining a first interior portion of the ear warmer shell, said first ear membrane being attached within the first interior portion;

a second ear membrane attached to said outer membrane along a second portion of the perimeter and defining a second interior portion of the ear warmer shell, said second ear membrane being attached within the second interior portion;

a middle membrane attached to said outer membrane along a third portion of the perimeter and defining a third interior portion of the ear warmer shell, said first ear membrane being attached within the third interior portion.

13. The ear warmer shell of claim 12, wherein:

the first ear membrane further includes a central portion and a plurality of extended portions, an attachment of the first ear membrane to the outer membrane being disposed between the central portion and the plurality of extended portions of the first ear membrane; and the second ear membrane further includes a central portion and a plurality of extended portions, the attachment of the second ear membrane to the outer membrane being disposed between the central portion and the plurality of extended portions of the second ear membrane.

14. The ear warmer shell of claim 12, further comprising:

a first pocket membrane disposed within the first interior portion between an end of the first ear membrane and a first end of the outer membrane; and a second pocket membrane disposed within the second interior portion between an end of the second ear membrane and a second end of the outer membrane.

15. The ear warmer shell of claim 14, further comprising:

a first frame member disposed within the first interior portion, an end of the first frame member being disposed within a first pocket defined by the first pocket membrane and the first end of the outer membrane;

a second frame member disposed within the second interior portion, an end of the second frame member being disposed within a second pocket defined by the second pocket membrane and the second end of the outer membrane; and a third frame member having a first end and a second end, the first end of the third frame member being connected to a second end of the first frame member, the second end of the third frame member being connected to a second end of the second frame member.

16. The ear warmer of claim 15, wherein the third frame member is a band having a slidably adjustable length.

17. An ear warmer, comprising:

a plurality of membranes collectively defining an outer perimeter, the plurality of membranes being attached along the outer perimeter to define an attachment portion, the attachment portion being entirely disposed within an interior of the plurality of membranes; and a frame disposed within the interior of the plurality of membranes.

18. The ear warmer of claim 17, wherein said plurality of membranes includes:

an outer membrane;

a first ear membrane attached to said outer membrane along a first portion of the outer perimeter and defining a first interior portion of the ear warmer shell, said first ear membrane being attached within the first interior portion;

a second ear membrane attached to said outer membrane along a second portion of the outer perimeter and defining a second interior portion of the ear warmer shell, said second ear membrane being attached within the second interior portion;

a middle membrane attached to said outer membrane along a third portion of the outer perimeter and defining a third interior portion of the ear warmer shell, said first ear membrane being attached within the third interior portion.

19. The ear warmer of claim 17, wherein said plurality of membranes are attached along an entirety of the outer perimeter.

20. The ear warmer of claim 17, wherein the attachment portion of said plurality of membranes includes a sewn seam.

21. The ear warmer of claim 17, wherein said frame is disposed entirely within the interior of the plurality of membranes.

22. A method for assembling an ear warmer having a membrane with a plurality of membrane portions, the plurality of membranes including a first ear portion, a second ear portion, a middle portion and an outer portion, said method comprising:

folding the first ear portion and the second ear portion on to the outer portion;

folding the middle portion on to the outer portion;

attaching an outer perimeter of the plurality of membrane portions after the folding steps, the plurality of membrane portions defining a first ear portion, a second ear portion and a middle portion;

turning inside out the first ear portion through an opening of the first ear portion; and turning inside out the second ear portion through an opening of the second ear portion, through a channel of the middle portion and through the opening of the first ear portion.

23. The method of claim 22, further comprising:

inserting a first frame member into the first ear portion through the opening of the first ear portion;

inserting a second frame member into the second ear portion through the opening of the second ear portion; and inserting a third frame member into the channel of the middle portion.

24. The method of claim 23, further comprising:

disposing a first end of the first frame member adjacent to a first end of the third member through the opening of the first ear portion;

attaching the first end of the first frame member to the first end of the third frame member;

disposing a first end of the second frame member adjacent to a second end of the third member through the opening of the second ear portion; and attaching the first end of the second frame member to the second end of the third frame member.

25. The method of claim 23, wherein the third frame member is a band having a slidably adjustable length.

26. An ear warmer having an outer perimeter, comprising:
a plurality of membrane portions, the plurality of membrane portions being folded together to define the outer perimeter of the ear warmer, the plurality of membrane portions being attached along the outer perimeter of the ear warmer to define an attachment portion, the attachment portion being entirely disposed within an interior of the plurality of membrane portions; and
a frame disposed within the interior of the plurality of membrane portions.

27. The ear warmer of claim 26, wherein said plurality of membrane portions includes:
an outer membrane portion;
a first ear membrane portion being integrally formed with said outer membrane portion along a first portion of said first ear membrane portion, a second portion of said first ear membrane portion being attached to said outer membrane along a first portion of the outer perimeter and within a first interior portion of the ear warmer shell.

28. The ear warmer of claim 26, wherein said plurality of membrane portions includes:
an outer membrane portion;
a middle membrane portion being integrally formed with said outer membrane along a first portion of said middle membrane portion, a second portion of said middle membrane portion being attached to said outer membrane along a third portion of the outer perimeter and within the third interior portion.

29. The ear warmer of claim 26, wherein said plurality of membrane portions are attached along an entirety of the outer perimeter of the ear warmer shell.

30. The ear warmer of claim 26, wherein the attachment portion of said plurality of membrane portions includes a sewn seam.

31. The ear warmer of claim 26, wherein said frame is disposed entirely within the interior of the plurality of membrane portions.

* * * * *

UNITED STATES PATENT AND TRADEMARK OFFICE
CERTIFICATE OF CORRECTION

PATENT NO.    : 6,332,223 B1
DATED         : December 25, 2001
INVENTOR(S)   : Brian Edward Le Gette and Justin Saul Werner It is certified that error appears in the above-identified patent and that said Letters Patent is hereby corrected as shown below:

Title page,
Item [56], References Cited, U.S. PATENT DOCUMENTS should include:

| Patent No. | Date | Inventor | Class |
|---|---|---|---|
| 548,738 | 10/1895 | Ballard | |
| 1,179,473 | 4/1916 | Taylor | |
| 1,326,875 | 12/1919 | Miller | |
| 1,398,958 | 12/1921 | Basch | |
| 1,628,483 | 5/1927 | Wiegand et al. | |
| 2,070,216 | 2/1937 | Rosenberg | 2/209 |
| 2,246,031 | 6/1941 | Bartiz et al. | 2/209 |
| 2,314,782 | 3/1943 | Goretsky | 2/209 |
| 2,532,852 | 12/1950 | Oaks | 128/151 |
| 2,586,644 | 2/1952 | Gilbert | 179/156 |
| 2,615,169 | 10/1952 | Maxant | 2/209 |
| 2,717,930 | 9/1955 | Hintz | 179/156 |
| 3,249,949 | 5/1966 | Rosenberg et al. | 2/209 |
| 3,308,480 | 3/1967 | Elder | 2/209 |
| 3,447,160 | 6/1969 | Teder | 2/209 |
| 3,509,580 | 5/1970 | Rubenstein et al. | 2/65 |
| 3,787,899 | 1/1974 | Krawagna | 2/209 |
| 4,277,847 | 7/1981 | Florio | 2/12 |
| 4,404,434 | 9/1983 | Pelt et al. | 179/156 |
| 4,463,223 | 7/1984 | Yamanoi et al. | 179/156R |
| 4,516,274 | 5/1985 | Buckland | 2/209 |
| 4,546,215 | 10/1985 | Ferraro | 179/156 |
| 4,654,898 | 4/1987 | Ishikawa | 2/209 |
| 4,669,129 | 6/1987 | Chance | 2/209 |
| 4,670,911 | 6/1987 | Dunford | 2/209 |
| 4,727,599 | 2/1988 | Rappaport et al. | 455/351 |
| 4,776,042 | 10/1988 | Hanson et al. | 2/7 |
| 4,776,044 | 10/1988 | Makins | 2/209 |
| 4,791,684 | 12/1988 | Schwartz | 2/209 |
| 4,858,248 | 8/1989 | Goldsmith et al. | 2/209.1 |
| 4,864,619 | 9/1989 | Spates | 381/25 |
| 4,918,757 | 7/1990 | Janssen et al. | 2/171 |
| 4,982,451 | 1/1991 | Graham | 2/410 |
| 5,038,412 | 8/1991 | Cionni | 2/209 |
| 5,117,464 | 5/1992 | Jones et al. | 381/183 |
| 5,164,987 | 11/1992 | Raven | 381/25 |
| 5,201,856 | 7/1993 | Edwards | 2/209 |
| 5,257,420 | 11/1993 | Byrne, Jr. | 2/209 |
| 5,327,178 | 7/1994 | McManigal | 351/158 |
| 5,835,609 | 11/1998 | LeGette et al. | 381/187 |

UNITED STATES PATENT AND TRADEMARK OFFICE
CERTIFICATE OF CORRECTION

PATENT NO. : 6,332,223 B1
DATED : December 25, 2001
INVENTOR(S) : Brian Edward Le Gette and Justin Saul Werner It is certified that error appears in the above-identified patent and that said Letters Patent is hereby corrected as shown below:

<u>Title page (cont'd),</u>
Item [56], References Cited, FOREIGN PATENT DOCUMENTS should include:

| | | |
|---|---|---|
| 294003 | 1/1954 | (CH) |
| 1353524 | 1/1964 | (FR) |
| 2532838 | 3/1984 | (FR) |
| 2536253 | 5/1984 | (FR) |
| 0745364 A3 | 12/1996 | (EP) |

<u>Column 10,</u>
Line 8, delete "shell";
Line 14, delete "shell";
Line 32, replace "membranes" with -- membrane portions --;
Line 58, insert -- frame -- after "third";
Line 63, insert -- frame -- after "third";

<u>Column 11,</u>
Line 22, insert -- portion -- after "membrane";

<u>Column 12,</u>
Line 2, delete "shell";
Line 7, add -- portion -- after "membrane";
Line 10, add -- portion -- after "membrane";
Line 11, delete "third" and delete "portion"; and
Line 14, delete "shell".

Signed and Sealed this

Twenty-third Day of March, 2004

JON W. DUDAS
*Acting Director of the United States Patent and Trademark Office*